US00PP13043P2

(12) United States Plant Patent
Drewlow

(10) Patent No.: US PP13,043 P2
(45) Date of Patent: Oct. 1, 2002

(54) NEW GUINEA IMPATIENS PLANT NAMED 'OVATION BLUSH ROSE'

(75) Inventor: Lyndon W. Drewlow, Lompoc, CA (US)

(73) Assignee: Oglevee Ltd., Connellsville, PA (US)

( * ) Notice: Subject to any disclaimer, the term of this patent is extended or adjusted under 35 U.S.C. 154(b) by 0 days.

(21) Appl. No.: 09/876,934

(22) Filed: Jun. 11, 2001

(51) Int. Cl.[7] ..... A01H 5/00
(52) U.S. Cl. ..... Plt./318

(58) Field of Search ..... Plt./318

*Primary Examiner*—Bruce R. Campell
*Assistant Examiner*—Annette H. Para
(74) *Attorney, Agent, or Firm*—C. A. Whealy

(57) ABSTRACT

A new and distinct cultivar of New Guinea Impatiens plant named 'Ovation Blush Rose', characterized by its very large and rounded pink-colored flowers; freely flowering habit with flowers positioned above or beyond the foliage; mounded plant habit; freely branching growth habit; red purple-colored leaves; and tolerance to full sun conditions and high and low temperatures.

1 Drawing Sheet

BOTANICAL CLASSIFICATION

*Impatiens hawkeri* cultivar Ovation Blush Rose.

BACKGROUND OF THE INVENTION

The present Invention relates to a new and distinct cultivar of New Guinea Impatiens plant, botanically known as *Impatiens hawkeri*, and hereinafter referred to by the cultivar name Ovation Blush Rose.

The new Impatiens is a product of a planned breeding program conducted by the Inventor in Ashtabula, Ohio. The objective of the breeding program is to develop new intermediate-sized New Guinea Impatiens cultivars with numerous large rounded flowers and interesting flower and foliage colors.

The new Impatiens originated from a cross made by the Inventor during the winter of 1996/1997 of a proprietary *Impatiens hawkeri* seedling selection designated as code number 96-1230-1, not patented, as the female, or seed parent, with a proprietary *Impatiens hawkeri* seedling selection designated as code number 96-1238-30, not patented, as the male, or pollen parent. The cultivar Ovation Blush Rose was discovered and selected by the Inventor as a flowering plant within the progeny of the stated cross in controlled environment in Ashtabula, Ohio.

Asexual reproduction of the new cultivar by terminal cuttings taken at Ashtabula, Ohio, since May, 1997, has shown that the unique features of this new Impatiens are stable and reproduced true to type in successive generations. Plants of the new Impatiens differ from plants of the parent selections primarily in plant growth habit, flower shape and color.

SUMMARY OF THE INVENTION

The following traits have been repeatedly observed and are determined to be the unique characteristics of 'Ovation Blush Rose'. These characteristics in combination distinguish 'Ovation Blush Rose' as a new and distinct Impatiens cultivar:

1. Very large, rounded, pink-colored flowers with purple eye zone.

2. Freely flowering habit with flowers positioned above or beyond the foliage.
3. Mounded plant habit.
4. Freely branching growth habit.
5. Red purple-colored leaves.
6. Tolerant to full sun conditions and high and low temperatures.

Plants of the new Impatiens can be compared to plants of the cultivar Ovation Blush Pink, U.S. Plant Patent applied for. In side-by-side comparisons conducted by the Inventor in Lompoc, Calif., plants of the new Impatiens differ from plants of the cultivar Ovation Blush Pink, in the following characteristics:

1. Lower surfaces of leaves of the new Impatiens are grayed purple in color whereas lower surfaces of leaves of the cultivar Ovation Blush Pink are grayed green in color.
2. Flower color of the new Impatiens is slightly darker pink than flower color of plants of the cultivar Ovation Blush Pink.
3. Stigma color of the new Impatiens is red purple whereas stigma color of the cultivar Ovation Blush Pink is white.

Plants of the new Impatiens can also be compared to plants of the cultivar Improved Samoa, disclosed in U.S. Plant Pat. No. 9,138. In side-by-side comparisons conducted by the Inventor in Lompoc, Calif., plants of the new Impatiens differ from plants of the cultivar Improved Samoa, in the following characteristics:

1. Plants of the new Impatiens are more mounded and not as upright as plants of the cultivar Improved Samoa.
2. Lower surfaces of leaves of the new Impatiens are grayed purple in color whereas lower surfaces of leaves of the cultivar Improved Samoa are green in color.
3. Plants of the new Impatiens have slightly larger flowers than plants of the cultivar Improved Samoa.
4. Flower color of the new Impatiens is slightly darker pink than flower color of the cultivar Improved Samoa.
5. Stigma color of the new Impatiens is red purple whereas stigma color of the cultivar Improved Samoa is white.

BRIEF DESCRIPTION OF THE PHOTOGRAPH

The accompanying colored photograph illustrates the overall appearance of the new cultivar, showing the colors as true as it is reasonably possible to obtain in colored reproductions of this type. Colors in the photograph may differ slightly from the color values cited in the detailed botanical description which accurately describe the colors of the new Impatiens. The photograph comprises a top perspective view of a typical flowering plant of 'Ovation Blush Rose' grown during the winter in Lompoc, Calif., in a 15-cm container for about 8 to 10 weeks after planting a rooted cutting.

DETAILED BOTANICAL DESCRIPTION

The cultivar Ovation Blush Rose has not been observed under all possible environmental conditions. The phenotype may vary somewhat with variations in environment such as temperature, light intensity, daylength, water status and/or fertilizer type or rate, without, however, any variance in genotype. The following observations and measurements describe plants grown in Lompoc, Calif., during the winter, under commercial practice in a fiberglass-covered greenhouse. Plants used in the following description were grown in 15-cm containers for about 8 to 10 weeks after planting rooted cuttings. During the production period, day temperatures ranged from 21 to 24° C., night temperatures ranged from 16 to 18° C., and light levels ranged from 3,000 to 4,000 foot-candles.

In the following description, color references are made to The Royal Horticultural Society Colour Chart except where general terms of ordinary dictionary significance are used.

Botanical classification: *Impatiens hawkeri* cultivar Ovation Blush Rose.

Commercial classification: New Guinea Impatiens cultivar Ovation Blush Rose.

Parentage:

*Female parent.*—Proprietary *Impatiens hawkeri* seedling selection designated as code number 96-1230-1, not patented.

*Male parent.*—Proprietary *Impatiens hawkeri* seedling selection designated as code number 96-1238-30, not patented.

Propagation:

*Type cutting.*—Terminal cuttings.

*Time to initiate roots.*—Summer: About 10 days at 21° C. Winter: About 12 days at 21° C.

*Time to produce a rooted cutting.*—Summer and winter: About 21 days at 21° C.

*Root description.*—Numerous, white, fine, fibrous and freely branching.

Plant description:

*General appearance.*—Mounded plant habit, intermediate in size.

*Growth and branching habit.*—Freely branching and densely foliated, typically more than 10 lateral branches per plant develop; pinching, that is, removal of the terminal apices, is typically not required. Vigorous growth habit.

*Crop time.*—To produce a finished flowering plant in a 15-cm container: About 8 to 10 weeks from a rooted cutting. To produce a finished flowering plant in a 25-cm container: About 10 to 12 weeks from a rooted cutting.

*Plant height.*—About 17.5 cm.

*Plant spread.*—About 32.5 cm.

*Lateral branch description.*—Length: About 10 to 15 cm. Diameter: About 8 to 10 mm. Internode length: About 3 to 4 cm. Texture: Smooth, glabrous. Color: 146B overlain with 59B.

*Foliage description.*—Arrangement: Alternate or in whorls of five. Length, mature leaves: About 12.5 cm. Width, mature leaves: About 4.5 cm. Shape: Lanceolate. Apex: Acuminate. Base: Acute. Margin: Serrulate with fine ciliation. Texture: Smooth, glabrous. Venation pattern: Pinnate. Color: Young foliage, upper surface: 147A, overlain with 59B. Young foliage, lower surface: 59B. Fully expanded foliage, upper surface: 147A, overlain with 59B. Fully expanded foliage, lower surface: 183B. Venation, upper surface: 147B. Venation, lower surface: 185B. Petiole: Length: About 1.2 cm. Diameter: About 3 mm. Texture: Smooth, glabrous. Color: 185B.

Flower description:

*Flower type and flowering habit.*—Single, large and rounded pink flowers with purple eye zone. Freely flowering, usually one flower per leaf axil and about 5 flowers and flower buds per lateral branch. Flowers positioned above and beyond the foliage and typically face upward or outward. Flowers flat when fully opened. Flowers last about two weeks on the plant depending on environmental conditions. Petals self-cleaning; gynoecium persistent. Flowers not fragrant. Flowering indeterminate and continuous.

*Flowering season.*—Year-round under greenhouse conditions. In the garden, flowering from spring until fall.

*Flower diameter.*—About 7.5 cm.

*Flower buds.*—Rate of opening: From flower bud to fully open flower, typically about 5 to 7 days depending on temperature. Length: About 2.5 cm. Diameter: About 1.5 cm. Shape: Ellipsoidal. Texture: Smooth, glabrous. Color, just before opening: 56A.

*Petals.*—Quantity: Single, five per flower, imbricate. Length: About 3.5 cm. Width: About 5 cm. Shape: Roughly cordate. Apex: Emarginate. Base: Rounded, obtuse. Margin: Entire. Texture: Smooth; satiny. Color: Upper surface, when opening and fully opened: 56A, fading to 56B with subsequent development; eye zone, 58B. Lower surface, when opening and fully opened: 62C; midrib of banner petal, 58B.

*Spur.*—Length: About 5 cm. Texture: Smooth, glabrous. Color: 184B, green towards apex.

*Peduncles.*—Length: About 5 cm. Strength: Strong, flexible. Aspect: About 45° from the stem. Color: 146C.

*Reproductive organs.*—Androecium: Stamen number: Five fused at anthers, filaments free, hooded. Anther shape: Obovate. Anther length: About 5 mm. Anther color: 58B. Amount of pollen: Abundant. Pollen color: White. Gynoecium: Pistil number: One. Pistil length: About 5 mm. Stigma shape: Columnar, five-segmented. Stigma color: Red purple. Style color: Red purple. Ovary color: Green with red cast.

*Seed development.*—Seed development has not been observed.

Disease tolerance: Plants of the new Impatiens have been observed to be tolerant to pathogens common to Impatiens, such as Botrytis.

Temperature and light tolerance: In Connellsvile, Pa., plants of the new Impatiens have been observed to be tolerant to full sun conditions and high temperatures, 32 to 38° C., during the summer and continue to flower. In Lompoc, Calif., plants of the new Impatiens have been observed to be tolerant to low night temperatures, about 5 to 10° C., and to continue to flower.

It is claimed:

1. A new and distinct cultivar of New Guinea Impatiens plant named 'Ovation Blush Rose', as illustrated and described.

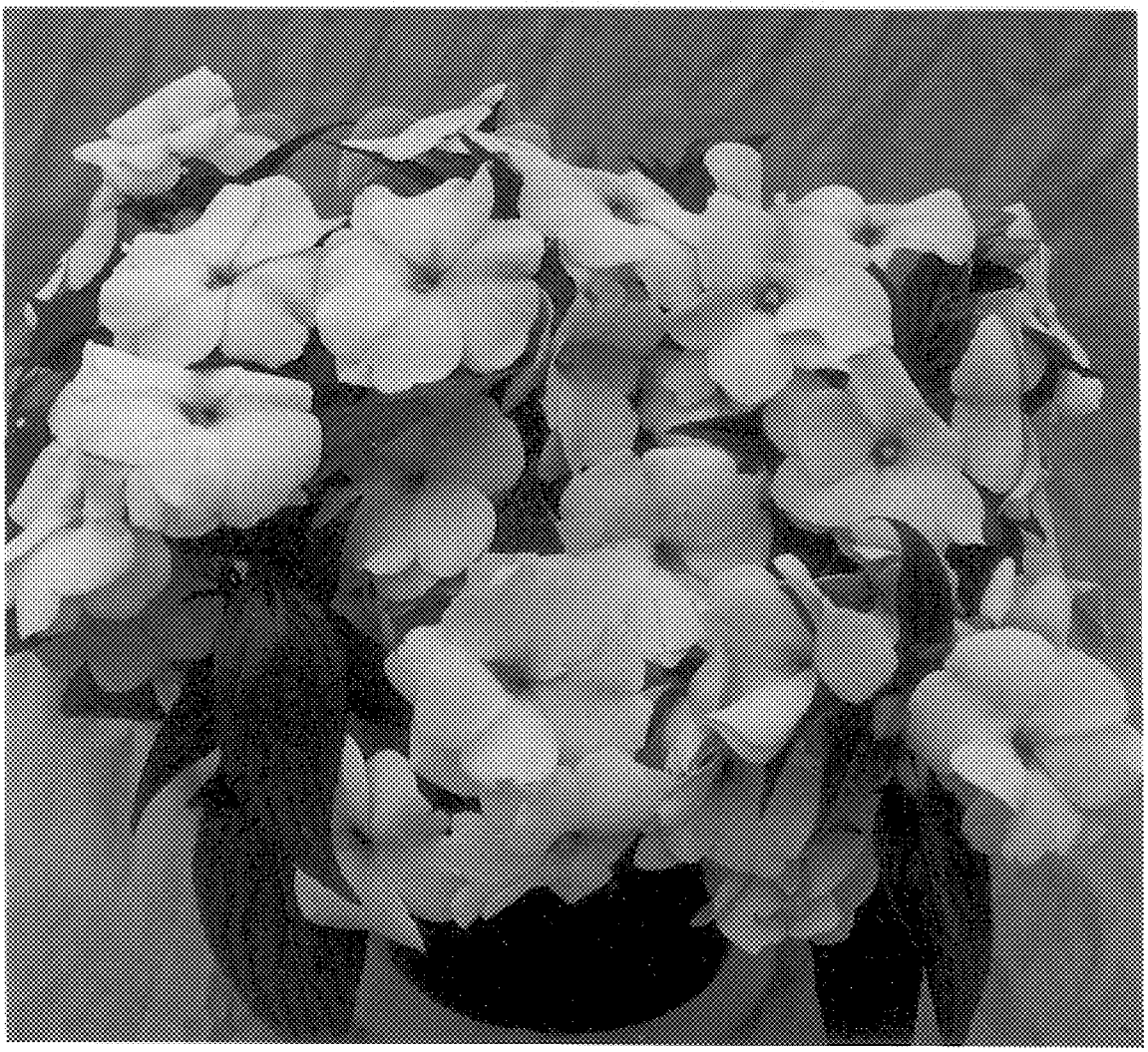

* * * * *